United States Patent
Sicking

(10) Patent No.: US 10,444,099 B2
(45) Date of Patent: Oct. 15, 2019

(54) SYSTEMS AND METHODS FOR TESTING PROTECTIVE HELMETS

(71) Applicant: THE UAB RESEARCH FOUNDATION, Birmingham, AL (US)

(72) Inventor: Dean Sicking, Indian Springs Village, AL (US)

(73) Assignee: UAB Research Foundation, Birmingham, AL (US)

( * ) Notice: Subject to any disclaimer, the term of this patent is extended or adjusted under 35 U.S.C. 154(b) by 349 days.

(21) Appl. No.: 15/036,444

(22) PCT Filed: Nov. 14, 2014

(86) PCT No.: PCT/US2014/065802
§ 371 (c)(1),
(2) Date: May 13, 2016

(87) PCT Pub. No.: WO2015/073893
PCT Pub. Date: May 21, 2015

(65) Prior Publication Data
US 2016/0290881 A1  Oct. 6, 2016

Related U.S. Application Data

(60) Provisional application No. 61/904,165, filed on Nov. 14, 2013.

(51) Int. Cl.
*G01M 7/08* (2006.01)
*G01N 3/30* (2006.01)
*G01L 5/00* (2006.01)
*A42B 3/06* (2006.01)

(52) U.S. Cl.
CPC ............. *G01L 5/0052* (2013.01); *G01M 7/08* (2013.01); *A42B 3/06* (2013.01); *G01N 3/30* (2013.01)

(58) Field of Classification Search
USPC ....................................................... 73/12.04
See application file for complete search history.

(56) References Cited

U.S. PATENT DOCUMENTS

| 171,769 A | 1/1876 | Buel |
| 4,674,911 A | 6/1987 | Gertz |
| 5,623,094 A | 4/1997 | Song et al. |

(Continued)

FOREIGN PATENT DOCUMENTS

| JP | 08170676 A | * | 7/1996 |
| JP | 09049780 A | * | 2/1997 |
| JP | 2007240402 A | * | 9/2007 |

OTHER PUBLICATIONS

International Search Report for PCT/US2014/065802 dated Apr. 9, 2015.

*Primary Examiner* — Matthew G Marini
*Assistant Examiner* — Ruben C Parco, Jr.
(74) *Attorney, Agent, or Firm* — Thomas | Horstemeyer, LLP

(57) ABSTRACT

In one embodiment, a helmet testing system includes a sled adapted to support a bullet dummy, a track along which the sled can travel, a target dummy support apparatus adapted to support a target dummy at a point near an end of the track, and an impact cushion positioned at the end of the track that is adapted to halt forward motion of the sled along the track to enable the bullet dummy to be launched from the sled and into the target dummy.

14 Claims, 4 Drawing Sheets

(56) References Cited

U.S. PATENT DOCUMENTS

| | | | |
|---|---|---|---|
| 5,688,196 A | 11/1997 | O'Neil | |
| 6,422,058 B1* | 7/2002 | Myles | G01M 17/0078 |
| | | | 73/12.04 |
| 6,609,409 B1 | 8/2003 | Bock et al. | |
| 2005/0155441 A1* | 7/2005 | Nagata | G01M 17/0078 |
| | | | 73/865.3 |
| 2008/0016970 A1* | 1/2008 | Klein | G01M 17/0078 |
| | | | 73/865.3 |
| 2013/0147117 A1* | 6/2013 | Graham | F41J 7/04 |
| | | | 273/393 |

* cited by examiner

SYSTEMS AND METHODS FOR TESTING PROTECTIVE HELMETS

CROSS-REFERENCE TO RELATED APPLICATION

This application is the 35 U.S.C. § 371 national stage application of PCT Application No. PCT/US2014/065802, filed Nov. 14, 2014, which claims priority to U.S. Provisional Application Ser. No. 61/904,165, filed Nov. 14, 2013, both of which are hereby incorporated by reference herein in their entireties.

BACKGROUND

Contact sports, such as American football, hockey, baseball, and lacrosse, require the use of protective helmets to decrease the likelihood of head injury while playing the sport. Modern helmets are generally comprised of four features: a plastic outer shell, a liner typically comprising a shock absorbing material and air, a metal facemask, and a chin strap.

The National Operating Committee on Standards for Athletic Equipment (NOCSAE) has established standards for testing football helmets. Early test standards were directed at measuring linear accelerations in a head form while outfitted with a helmet. During testing, the helmeted head form is struck with an impact force at different head orientations. More particularly, the helmeted head form is suspended above a metal and rubber block before being released to cause it to strike the block after free falling from a noted height. More recent test standards have been developed that measure both linear and rotational acceleration forces in a head form. In one such test, a striking force is imparted to a helmeted head form mounted on an adjustable platform via weighted pendulum.

These standards and methods only represent the player's head. Therefore, the helmets are not tested using the full mass and dynamics of the human body behind it. In addition, the effects of the presence of other safety equipment, such as shoulder pads, are not considered. Furthermore, the tests do not measure forces and moments in the neck that are caused by impact forces when the helmeted head is struck.

From the above discussion, it can be appreciated that it would be desirable to have a system and method for testing protective helmets that more accurately reflects the impacts experienced in the real world when playing a sport.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a system and method for testing protective helmets that more accurately reflects the impacts experienced in the real world when playing a sport. Embodiments of such systems and methods are disclosed herein. In some embodiments, a helmet testing system generally comprises a sled on which a bullet dummy is supported and a platform on which a target dummy is supported. The sled and the bullet dummy can be propelled toward the platform and the target dummy along a sled track at a speed that is sufficient to replicate the forces typically associated with a sports impact. Before reaching the platform, the forward motion of the sled is abruptly halted, thereby launching the bullet dummy into the target dummy. This dummy-dummy impact enables more accurate replication of on-field impact conditions. Each dummy can be fully instrumented so that the forces of the impact can be determined. In addition, each dummy can have a size, weight, and anatomical configuration that emulates that of a human being of a sport for which the helmets are being tested. Furthermore, each dummy can be oriented in nearly any human configuration prior to impact such that nearly any in-game impact condition can be recreated. Through such testing, protective helmets, as well as other protective equipment, can be evaluated for its effectiveness in preventing injury.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
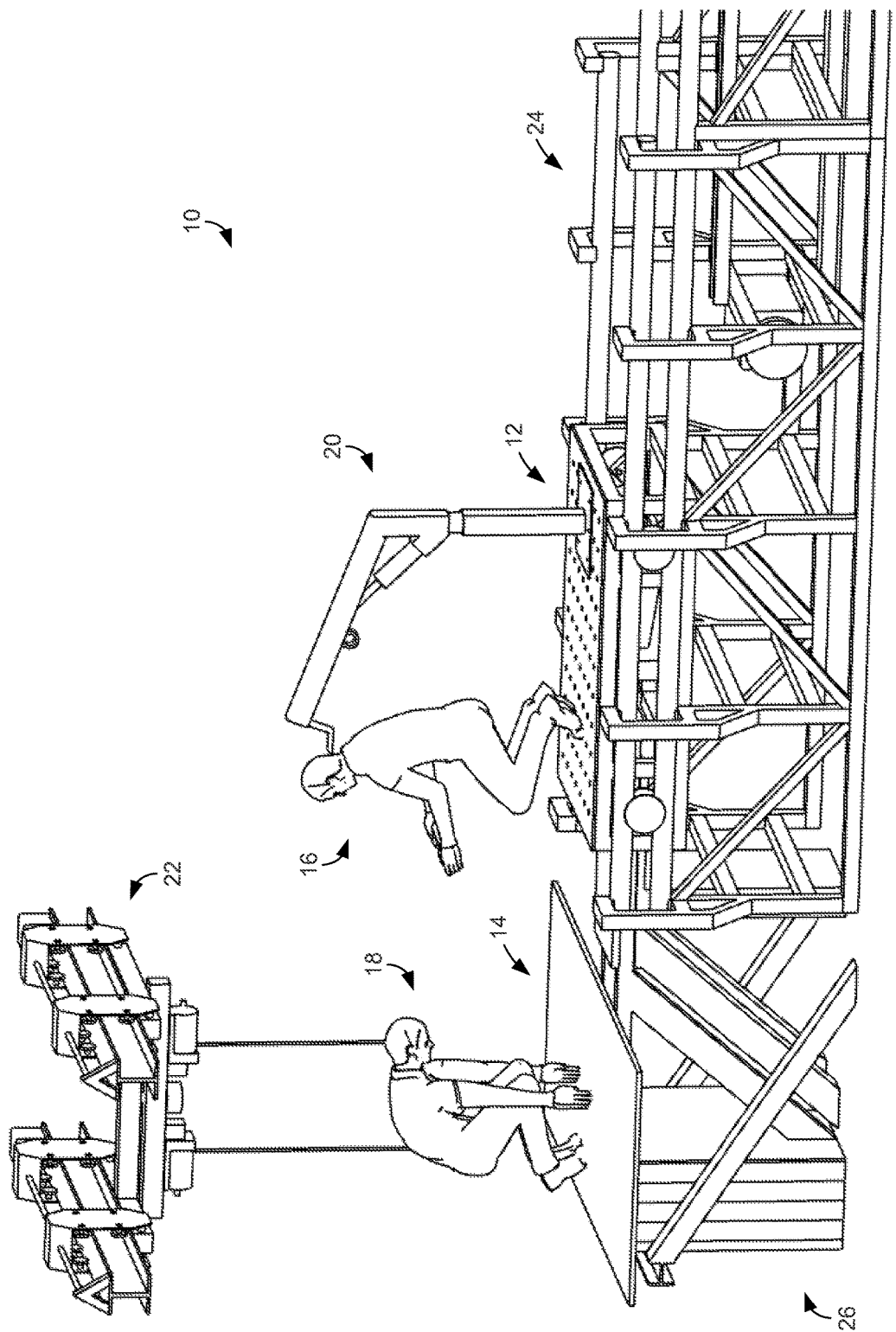
FIG. 1 is a perspective view of an embodiment of a system for testing protective helmets.

FIG. 1 illustrates an embodiment of a helmet testing system 10. While the system 10 is described as a "helmet" testing system, it will be appreciated from the discussions that follow that the system can be used to test other protective equipment as well. As indicated in FIG. 1, the system 10 generally includes a bullet dummy sled 12 and a target dummy platform 14 on which a bullet dummy 16 and a target dummy 18 are respectively supported. As noted above, each dummy 16, 18 can be fully instrumented such that parameters of each impact can be measured. In some embodiments, each dummy 16, 18 includes linear accelerometers and angular rate sensors provided within their heads, and load cells provided in their necks to measure neck forces and moments. As is also noted above, each dummy 16, 18 can have a size, weight, and anatomical configuration similar to that of a human being who would play the sport for which the testing is being performed. In some embodiments, the dummies 16, 18 are Hybrid III crash test dummies. Although not illustrated in the figure, each dummy can be provided with a protective helmet that covers the dummy's head as well as other equipment worn when playing the underlying sport.

The sled 12 is described below in detail in relation to FIGS. 4 and 5. It suffices to say at this point, however, that a bullet dummy support apparatus 20 is mounted to the sled 12. As is described below in relation to FIG. 5, this support apparatus 20 is an adjustable apparatus that can be used to place the bullet dummy 16 in substantially any desired position and orientation on top of the sled 12.

The platform 14 can comprise a metal plate that is strong enough to support the full weight of the target dummy 18.

The target dummy 18 is supported on the platform 14 by a target dummy support apparatus 22. Like the bullet dummy support apparatus 20, the target dummy support apparatus 22 is an adjustable apparatus and therefore can be used to position the target dummy 18 in substantially any desired position and orientation on top of the platform 14. The target dummy support apparatus 22 is described in detail below in relation to FIG. 6.

With further reference to FIG. 1, the helmet testing system 10 also includes a sled track 24 on which the sled 12 is supported and along with the sled can be propelled toward the platform 14. The track 24 is described in detail below in relation to FIG. 2.

With continued reference to FIG. 1, the system 10 further includes an impact cushion 26 positioned at the end of the sled track 24. The impact cushion 26 is adapted to halt forward motion of the bullet dummy sled 12 to enable the bullet dummy 16 to launch from the sled toward the target dummy 18. In the embodiment of FIG. 1, the impact cushion 26 supports the platform 14. The impact cushion 26 is described below in detail in relation to FIGS. 2 and 3.

Figure 2:
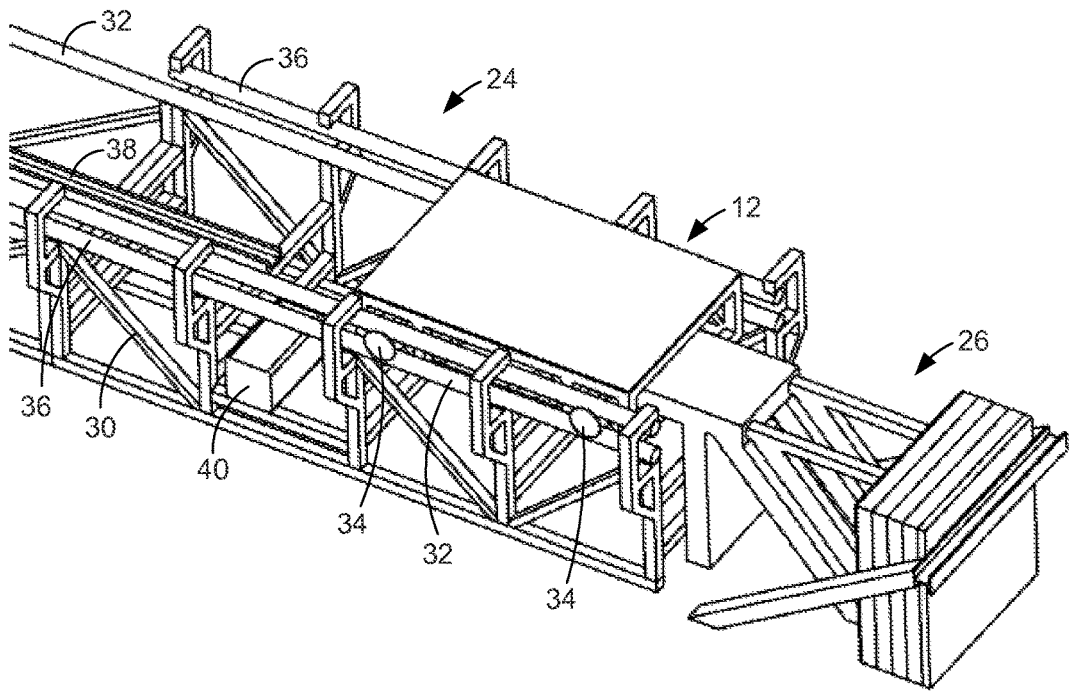
FIG. 2 is a perspective view of a sled track and an impact cushion of the system shown in FIG. 1.

FIG. 2 shows the sled 12, track 24, and impact cushion 26 with other apparatus of the system 10, including the platform 14 and the bullet dummy support apparatus 20, removed. As described above, the sled 12 is supported by the track 24 and can be propelled along its length. In some embodiments, the track 24 is many feet long to enable the sled 12 to reach the speed that is desired for the testing. In some embodiments, the track 24 can be constructed in segments that are connected together to achieve the desired track length.

As shown in FIG. 2, the track 24 generally comprises a frame 30 that supports two parallel, horizontal lower rails 32 that directly support the sled 12. More particularly, rollers 34 of the sled 12 are supported by the rails 32 to enable the sled to roll along the length of the track 24. In some embodiments, the track 24 further includes two parallel, horizontal upper rails 36 positioned at the end of the track near the impact zone (i.e., region in which the dummies 16,18 make contact) that ensure the sled does not leave the lower rails 32 when forward motion of the sled is halted by the impact cushion 26.

Also supported by the frame 30, at a central position between the lower rails 32, is a chain guide 38 that is adapted to guide a drive chain (not shown in FIG. 2) that is used to propel the sled 12 along the track 24. Further supported by the frame 30 is a drive motor 40 that is used to drive the chain. The motor 40 can comprise part of a sled drive system that further includes sprockets (not shown) around which the chains are wrapped.

As indicated in FIG. 2, the impact cushion 26 is positioned at the end of the sled track 24 within the impact zone. There, the impact cushion 26 can abruptly halt forward motion of the sled 12 to propel the bullet dummy 16 into the target dummy 18. The impact cushion 26 is shown separate from the track 24 in FIG. 3. As shown in this figure, the impact cushion 26 generally comprises four primary components: an impact member 44, an impact member support 46, energy absorbing padding 48, and a backstop 50. The impact member 44 comprises a frame 52 that includes two parallel, horizontal beams 54 that extend toward the track 24. Mounted to the ends of the beams 54 nearest the track 24 is an impact head 56 that the sled 12 directly impacts. Mounted to the opposite ends of the beams 54 is a force distribution plate 58 that distributes the forces transmitted by the beams upon sled impact. In the illustrated embodiment, the frame 52 of the impact member 44 further includes legs 60 that extend downward from the beams 54 and that are also connected to the plate 58. Each component of the impact member 44, including the frame 52, the impact head 56, and the plate 58 can be made of a strong metal material, such as steel.

Figure 3:
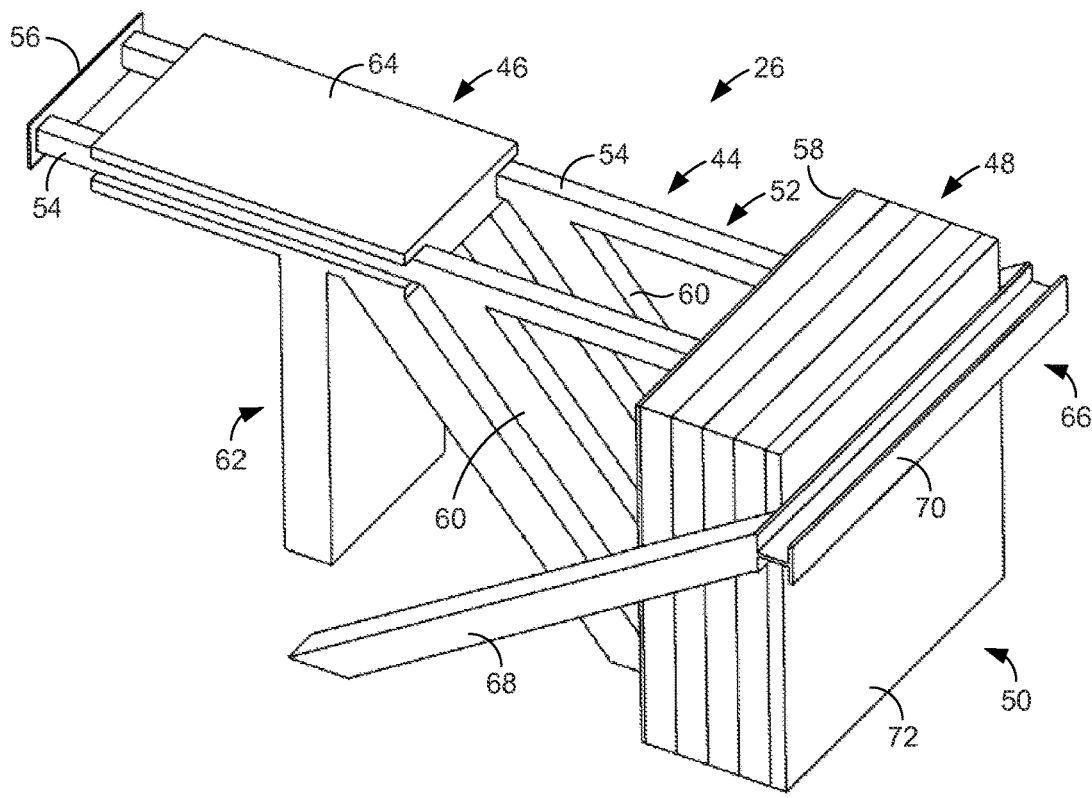
FIG. 3 is a perspective view of the impact cushion shown in FIGS. 1 and 2.

The impact member support 46 supports the impact member 44 and maintains it in the correct orientation during sled impact. As shown in FIG. 3, the impact member support 46 includes a frame 62 and a beam guide 64 that is supported by the frame. The beam guide 64 guides the beams 54 when they are displaced by a sled impact. Like the impact member 44, the impact member support 46 can be made of a strong metal material, such as steel. Unlike the impact member 44, the impact member support 46 is fixed in place. For example, the impact member support 46 can be bolted to the floor to ensure that it does not move.

The energy absorbing padding 48 is positioned between the force distribution plate 58 of the impact member 44 and the backstop 50. As its name suggests, the energy absorbing padding 48 absorbs the kinetic energy of the impact member 44 as it is displaced because of a sled impact. In some embodiments, the padding 48 comprises high-density foam padding.

The backstop 50 acts as a barrier that limits displacement of the impact member 44 and the padding 48. In the illustrated embodiment, the backstop 50 comprises a frame 66 that includes lateral beams 68, a medial beam 70, and a back plate 72. Both the lateral beams 68 and back plate 72 can also be bolted to the floor to ensure that the backstop 50 will not move. Each component of the backstop 50 can be also made of a strong metal material, such as steel.

When the sled 12 reaches the end of the sled track 24 during a test, it impacts the impact head 56 of the impact member 44. This impact substantially halts continued forward motion of the sled 12. Because of the momentum of the sled, this impact drives the horizontal beams 54 of the impact member 44 through the beam guide 64 like plungers, and the impact member is displaced toward the backstop 50. As a result, the force distribution plate 58 is pressed into the energy absorbing padding 48, which is supported by the back plate 72 of the backstop 50. Together, the padding 48 and the backstop 50 halt motion of the impact member 44.

Figure 4:
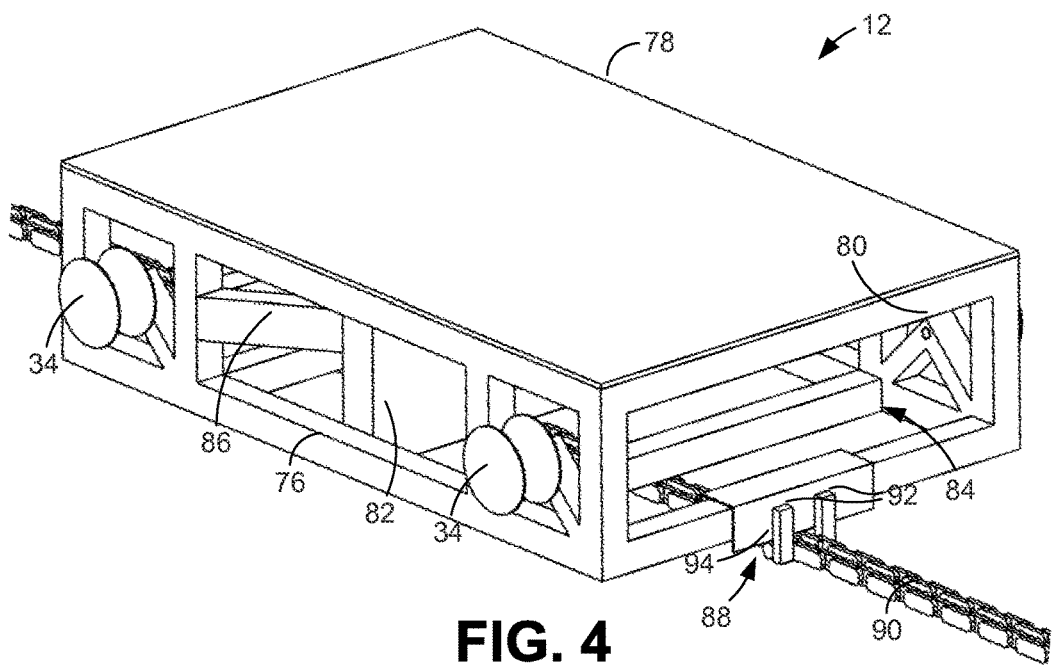
FIG. 4 is a perspective view of a bullet dummy sled and a drive chain of the system shown in FIG. 1.

FIG. 4 illustrates an embodiment of the sled 12. As shown in FIG. 4, the sled 12 comprises a frame 76 that supports the rollers 34 as well as a bullet dummy platform 78. Four such rollers 34 are provided, each being mounted to a side of the frame 76 with an axle 80 (only one axle identified in FIG. 4) that enables the roller to freely rotate. Within the frame 76 is an impact beam 82 that is adapted to impact the impact head 56 of the impact cushion 26 (FIG. 3). In particular, sled 12 is adapted to pass over the beams 54 of the impact member 44 of the impact cushion 26 until the impact beam 82 makes contact with the impact head 56. Stated otherwise, the frame 76 of the sled 12 receives the beams 54 of the impact member 44 through an opening 84 in the front of the frame. Bolstering the impact beam 80 are diagonal struts 86 that extend between the frame 76 and the impact beam 80. The frame 76, platform 78, and impact beam 82 can each be made of a strong metal material, such as steel.

With further reference to FIG. 4, attached to the frame 76 is a drive chain connection mechanism 88 that connects the sled 12 to a drive chain 90 that is used to propel the sled along the sled track 24. In the illustrated embodiment, the connection mechanism 88 comprises tangs 92 that extend down from the frame 76 and grip a dowel 94 that is mounted to the chain 90. With this configuration, the sled 12 is pulled forward when the chain 90 is driven forward by the aforementioned drive system. The connection mechanism 88, chain 90, and dowel 94 are each made of a strong metal material, such as steel.

Figure 5:
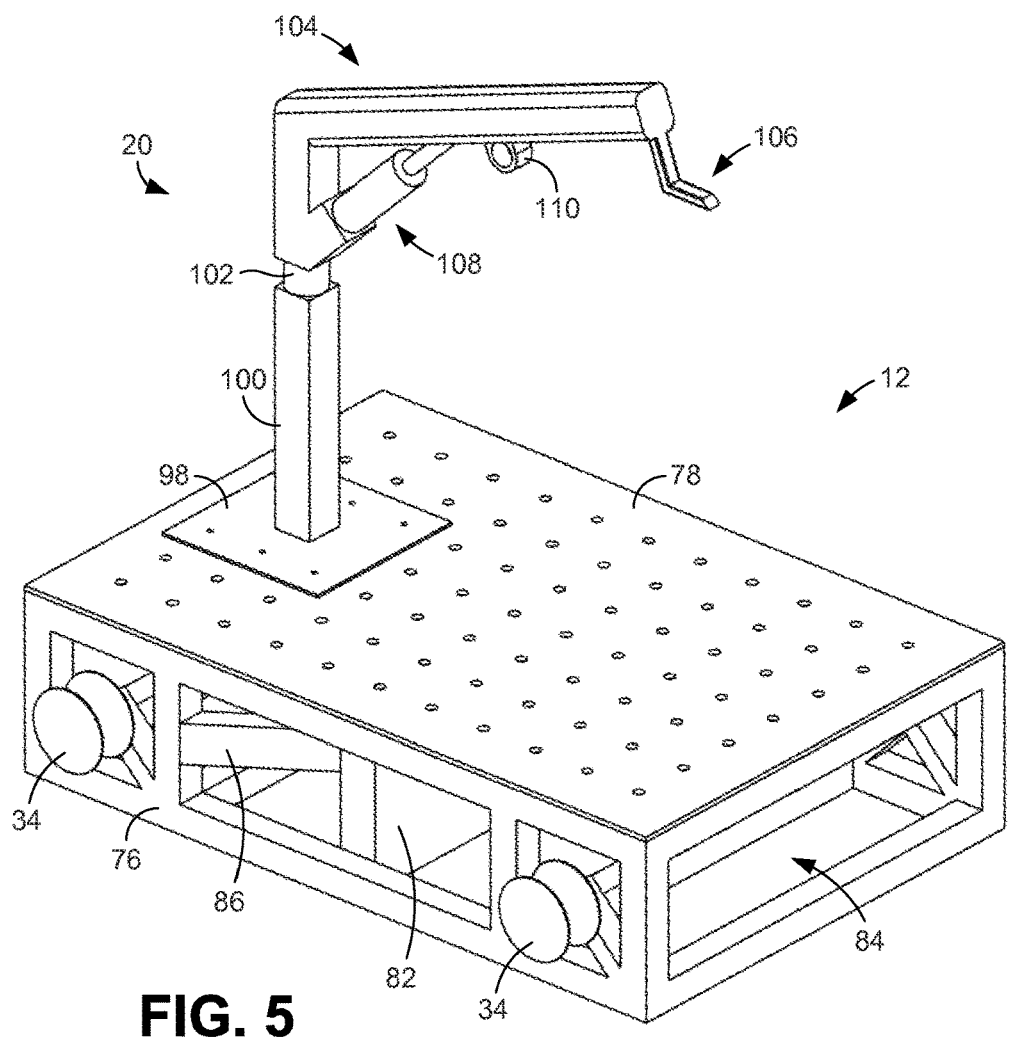
FIG. 5 is a perspective view of the bullet dummy sled shown in FIGS. 1 and 4 and a bullet dummy support apparatus mounted to the sled.

FIG. 5 shows the sled 12 without the chain connection mechanism 88 but with the bullet dummy support apparatus 20 attached. As shown in this figure, the apparatus 20 is mounted to the platform 78 of the sled 12 with a base plate 98. Extending upward from the base plate 98 is a vertical post 100 that receives a shaft 102 to which a boom arm 104 is mounted. The shaft 102 can rotate along its longitudinal axis relative to the post 100 to adjust the angular positioning of the boom arm 104 and, therefore, the bullet dummy 16. Provided at the end of the boom arm 104 is an adjustable hook 106 from which the bullet dummy 16 can be hung (see FIG. 1). The angle the boom arm 104 forms with the shaft 102, and therefore the height of the hook 106, can be adjusted using a lifting mechanism 108 that is connected to the boom arm. In the illustrated embodiment, the lifting mechanism 108 comprises a hydraulic jack. As is further illustrated in FIG. 5, an eyelet 110 is provided on the boom arm 104 to provide a further attachment point for the bullet dummy 16. As with other components described above, the base plate 98, post 100, shaft 102, and boom arm 104 can each be made of a strong metal material, such as steel.

Figure 6:
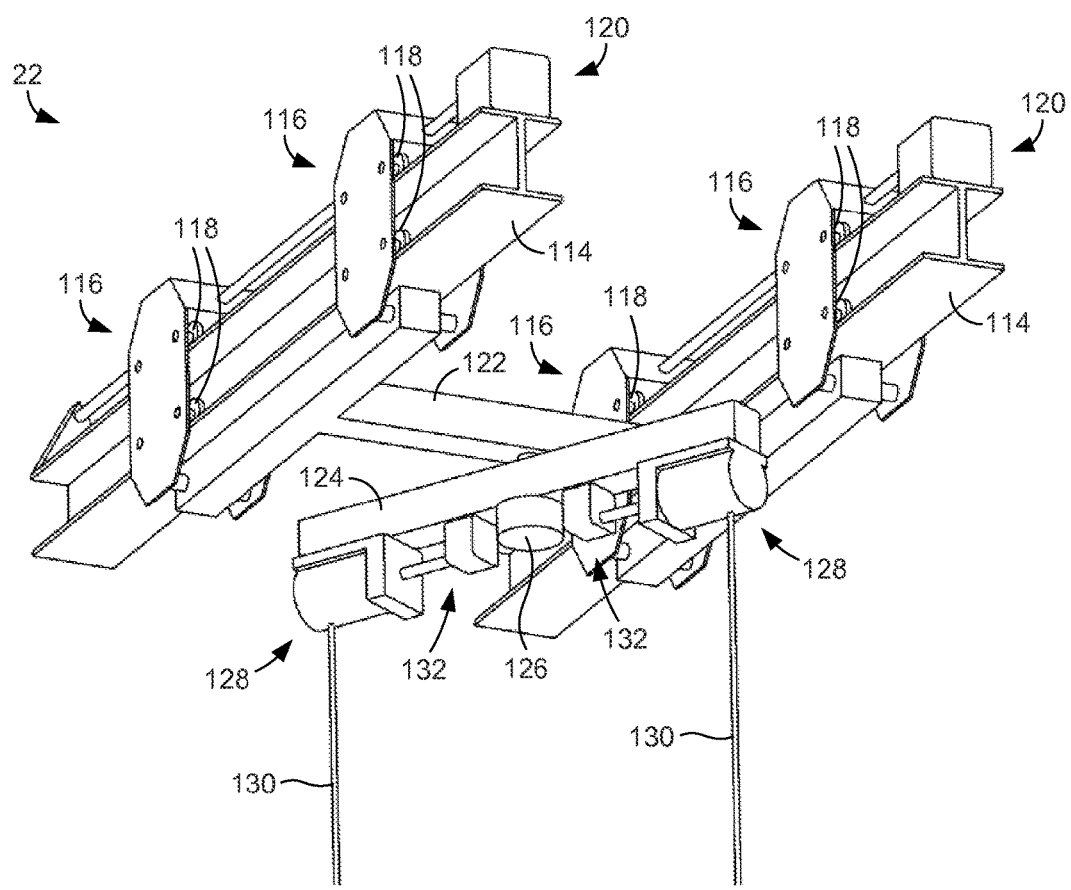
FIG. 6 is a perspective view of a target dummy support apparatus of the system shown in FIG. 1.

Referring next to FIG. 6, illustrated is the target dummy support apparatus 22, which can be mounted to the ceiling of the structure in which testing is performed. In the illustrated embodiment, the apparatus 22 includes two support beams 114, such as I-beams, that each support two trollies 116. The trollies 116 comprise rollers 118 that enable the trollies to slide along the lengths of the beams 114. In embodiments in which the support beams 114 are I-beams, each trolley 116 can have eight rollers, four that roll along the top horizontal plate of the beam and four that roll along the bottom horizontal plate of the beam. In some embodiments, a trolley positioning mechanism 120 is mounted to each support beam 114 that can be used to linearly displace the trollies 116 along the lengths of the beams 114. In some embodiments, the positioning mechanisms 120 comprise ball-and-screw mechanisms that each comprises a servomotor.

The four trollies 116 together support an H-shaped support bracket 122, which supports a winch bracket 124. Because it is supported by the trollies 116, the support bracket 122 can be displaced along the lengths of the support beams 114 with the trollies. In the illustrated embodiment, the winch bracket 124 mounts to the support bracket 122 at a single point about which the winch bracket 124 can be rotated under the control of a motor 126 that is connected to the winch bracket and the support bracket 122. Mounted to opposed ends of the winch bracket 124 are winches 128 that can be individually controlled to shorten or lengthen cables 130 from which the target dummy 18 is hung. Winch positioning systems 132 can be mounted to the winch bracket 124 in association with each winch 128. These systems 132 can be used to linearly displace the winches 128 along the length of the winch bracket 124. In some embodiments, the winch positioning systems 132 comprise ball-and-screw mechanisms that each comprises a servomotor. As shown in FIG. 1, the target dummy 18 can be supported from two points, including the head and the lower back. Eyebolts (not shown) can facilitate attachment of the cables 130 to the target dummy 18.

The helmet testing system 10 described above can be used to conduct testing of various protective helmets and other protective equipment. As an example, the bullet and target dummies 16, 18 can be arranged in orientations that replicate helmet-to-helmet collisions known to occur in their practical use. Such a collision can be recreated by accelerating the bullet dummy 16 down the track 24 on the sled 12. When the sled 12 crashes into the impact cushion 26, the bullet dummy 16 is launched into the target dummy 18. The instrumentation provided on the dummies 16, 18 collects all impact data, which can, for example, comprise three axes of linear and rotational accelerations within the heads of the dummies as well as three axes of forces and moments in/about the neck of the dummies.

The severity of on-field collisions is related to several impact characteristics including closing velocity, impact point on the helmet, player mass, and player body and head alignment. All of these parameters affect the peak g-loading and velocity change applied to a player's head during on-field impacts. The system 10 accurately represents these parameters by incorporating the full dynamics of a player's body and equipment mass, head/neck orientation, and back orientation by utilizing Hybrid III dummies.

Four types of Hybrid III dummies are available for testing: two 95th percentile weight class dummies and two 50th percentile weight class dummies. For any given test, two dummies can be selected to represent varying weight class pairings of on-field impacts. In the case of American football helmet testing, each test dummy can be outfitted with a football helmet, pads, cleats, and uniform.

Data from the instrumentation can be evaluated to determine the peak linear and rotational accelerations in the head, linear and rotational accelerations in the head throughout the duration of the impact, and change of velocity of the head over time. Force and moment data of the neck can also be measured over the duration of the impact to evaluate the amount of interaction between each dummy's head and neck during a helmet-to-helmet collision.

The helmet testing systems and methods of this disclosure have several advantages over current helmet testing devices and procedures, including: (1) inclusion of the mass of the dummy's body and other safety equipment, such as football pads, to accurately represent the full dynamics of a helmet-to-helmet collision; (2) adjustability in terms of velocity and dummy orientation to reconstruct a majority of on-field impacts; and (3) repeatability via electronic controls to ensure data accuracy.

While helmet-to-helmet impacts have been identified with particularity, it is noted that the disclosed systems can be used to obtain an accurate assessment of the weaponization of a helmet. Such testing can comprise propelling a bullet dummy into a rectangular polymer sheet that can provide a relatively consistent deformation profile. The peak deflection of the polymer provides a direct measure of the capability of a helmet to deliver a severe blow to an opponent.

The invention claimed is:

1. A protective helmet testing system comprising:
   a sled;
   a bullet dummy support apparatus mechanically coupled to the sled, the bullet dummy support apparatus including an adjustable boom arm adapted to support a bullet dummy, wherein adjusting the adjustable boom arm adjusts at least one of a height of the bullet dummy relative to the sled and an angular position of the bullet dummy relative to the sled;
   a track along which the sled can travel;
   a target dummy support apparatus adapted to support a target dummy at a point near an end of the track; and
   an impact cushion positioned at the end of the track that is adapted to halt forward motion of the sled along the track to enable the bullet dummy to be launched from the sled and into the target dummy, wherein the bullet dummy support apparatus further comprises a vertical post, wherein the adjustable boom arm comprises a rotatable shaft that is received in a first end of the vertical post, a second end of the vertical post being mechanically coupled to the sled, the rotatable shaft being capable of rotating along a longitudinal axis of the rotatable shaft to adjust the angular position of the adjustable boom arm and of the bullet dummy relative to the sled, wherein the bullet dummy support apparatus further comprises:

a hook at one end of the adjustable boom arm from which to hang the bullet dummy; and a lift mechanism coupled to the adjustable boom arm to adjust a height of the adjustable boom arm and the hook, thereby adjusting the height of the bullet dummy relative to the sled.

2. The system of claim 1, wherein the system includes the bullet dummy and the target dummy and wherein the dummies have sizes, weights, and configurations that emulate those of a human being.

3. The system of claim 2, wherein the dummies are equipped with sensors adapted to collect data associated with an impact between the dummies.

4. The system of claim 3, wherein the sensors include one or more of a linear accelerometer, an angular rate sensor, and a load cell.

5. The system of claim 1, wherein the sled comprises an impact beam adapted to impact the impact cushion.

6. The system of claim 1, wherein the track comprises a drive system that is adapted to drive the sled along the track.

7. The system of claim 6, wherein the drive system comprises a motor and a chain, wherein the sled is connected to the chain.

8. The system of claim 1, wherein the target dummy support apparatus comprises a cable from which the target dummy can be hung.

9. The system of claim 8, wherein the target dummy support apparatus further comprises a winch with which a length of the cable can be adjusted.

10. The system of claim 8, wherein the target dummy support apparatus further comprises a motor that can be used to adjust a position of the cable.

11. The system of claim 1, wherein the impact cushion comprises an impact head that the sled is adapted to impact.

12. The system of claim 11, wherein the impact head is mounted to a beam of an impact member that includes a force distribution plate.

13. The system of claim 12, wherein the impact cushion further comprises energy absorbing padding against which the plate can be pressed and a backstop that supports the padding.

14. The system of claim 1, wherein the impact cushion comprises a platform upon which the target dummy can be supported by the target dummy support apparatus.

* * * * *